United States Patent

Merkle et al.

[11] Patent Number: 6,066,761
[45] Date of Patent: May 23, 2000

[54] METHOD FOR ISOLATING 3-[2-CHLORO-4-(TRIFLUOROMETHYL)-PHENOXY]-BENZOIC ACID

[75] Inventors: Hans Rupert Merkle, Ludwigshafen, Germany; Ronald R. Eva, Bahama, N.C.; Dirk Franke, Ludwigshafen, Germany; Simon A. Jones, St. Ilgen, Germany; Wolfgang Mattmann, Limburgerhof, Germany; Manfred Munzinger, Dirmstein, Germany

[73] Assignee: BASF Aktiengesellschaft, Ludwigshafen, Germany

[21] Appl. No.: 09/355,277

[22] PCT Filed: Feb. 9, 1998

[86] PCT No.: PCT/EP98/00705

§ 371 Date: Jul. 28, 1999

§ 102(e) Date: Jul. 28, 1999

[87] PCT Pub. No.: WO98/37054

PCT Pub. Date: Aug. 27, 1998

[30] Foreign Application Priority Data

Feb. 21, 1997 [DE] Germany .............. 197 06 875

[51] Int. Cl.[7] ................................................. C07C 65/21
[52] U.S. Cl. ............................................. 562/474
[58] Field of Search ............................... 562/474

[56] References Cited

U.S. PATENT DOCUMENTS

| | | |
|---|---|---|
| 4,031,131 | 6/1977 | Johnson . |
| 4,076,741 | 2/1978 | Bayer et al. . |
| 4,400,530 | 8/1983 | Grove . |

FOREIGN PATENT DOCUMENTS 20 052  12/1980  European Pat. Off. .

*Primary Examiner*—Johann Richter
*Assistant Examiner*—Brian J. Davis
*Attorney, Agent, or Firm*—Keil & Weinkauf

[57] ABSTRACT

A process for the isolation of 3-[2-chloro-4-(trifluoromethyl)phenoxy]benzoic acid of the formula I

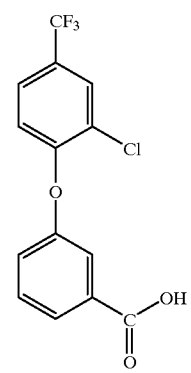

from an aqueous solution of its metal salt comprises a) reacting the metal salt of 3-[2-chloro-4-(trifluoromethyl)phenoxy]benzoic acid with an organic or inorganic acid;

b) heating the reaction mixture until a liquid two-phase system of organic and aqueous phase has formed; and c) separating the organic phase from the aqueous phase.

12 Claims, No Drawings

METHOD FOR ISOLATING 3-[2-CHLORO-4-(TRIFLUOROMETHYL)-PHENOXY]-BENZOIC ACID

This application is a 371 of PCT/EP98/00705 filed Feb. 9, 1998.

The present invention relates to a process for the isolation of 3-[2-chloro-4-(trifluoromethyl)pehnoxy]benzoic acid of the formula I

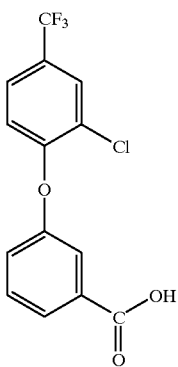

from an aqueous solution of its metal salt, which comprises a) reacting the metal salt of 3-[2-chloro-4-(trifluoromethyl)-phenoxy]benzoic acid with an organic or inorganic acid;

b) heating the reaction mixture until a liquid two-phase system of organic and aqueous phase has formed; and c) separating the organic phase from the aqueous phase.

3-[2-Chloro-4-(trifluoromethyl)phenoxy]benzoic acid of the formula I is an intermediate for the preparation of the herbicides acifluorfen, fluoroglycofen and lactofen, which are prepared in DE-A 23 11 638, EP-A 20 052, DE-A 30 29 728 and U.S. Pat. No. 4,031,131.

According to U.S. Pat. No. 4,031,131, the benzoic acid derivative of the formula I is precipitated from its salt solution in crystalline form by neutralization with an inorganic acid, isolated by filtration, washed with water and dried.

This process has a number of disadvantages: the handling of solids leads to the formation of crusts during the crystallization, causing the crystals to absorb significantly more water. During drying, this leads to clogging and to bottlenecks in the process.

It is an object of the present invention to provide a process for the isolation of the benzoic acid derivative of the formula I which does not have these disadvantages.

We have found that this object is achieved by the process described at the outset.

In U.S. Pat. No. 4,031,131, the preparation of the benzoic acid derivative of the formula I is carried out according to the following scheme:

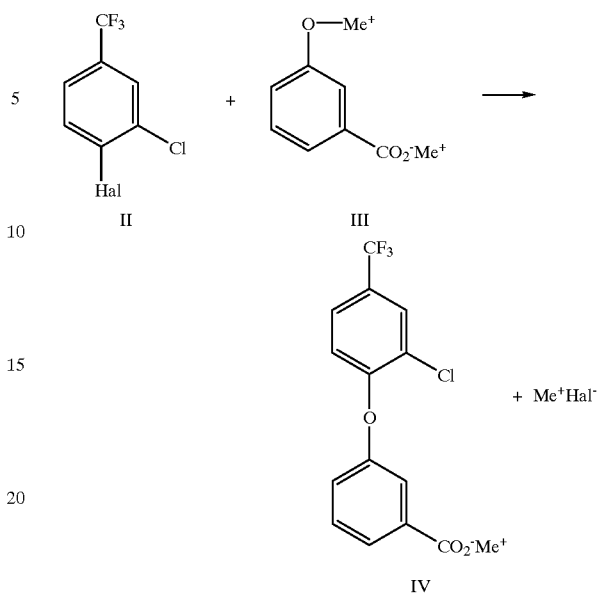

The trifluoromethylbenzene derivative of the formula II is reacted with the dimetal salt of 3-hydroxybenzoic acid to give the metal salt IV of the benzoic acid derivative.

In the process according to the invention, the isolation of the free acid of the benzoic acid derivative of the general formula I is carried out in three steps.

In step a), the aqueous solution of the metal salt of the benzoic acid derivative of the formula I is reacted with an organic or inorganic acid.

In principle, any monovalent or polyvalent metal salt $Me^+$ of the compound of the formula IV can be used as starting material. Preference is given to water-soluble metal salts.

Among the water-soluble metal salts, preference is given to the alkali metal salts. Particular preference is given to potassium and sodium salts.

All organic and inorganic acids are suitable for neutralizing the metal salts of the formula IV. Examples of suitable organic acids are formic acid, acetic acid, propionic acid and mixtures thereof. Preference is given to using acetic acid.

Suitable inorganic acids are hydrochloric acid, sulfuric acid, nitric acid, phosphoric acid and mixtures thereof.

The organic or inorganic acid is added to the aqueous solution of the metal salt of the formula IV with stirring at a temperature from 20 to 127° C., preferably 20 to 115° C., until a pH of less than 5, preferably less than 4.5, is obtained. This corresponds to approximately 1 to 6 times the molar amount of acid per mole of a metal salt of the formula IV, preferably 1 to 5 times the molar amount of acid. If the temperature is below about 90° C., the benzoic acid derivative I precipitates.

In step b) the reaction mixture is heated until the benzoic acid derivative I is molten and a liquid two-phase system of organic phase and aqueous phase has formed. The lower organic phase contains the molten benzoic acid derivative I. The temperatures in step b) are from 90 to 127° C., preferably from 95 to 115° C.

It is also possible to carry out steps a) and b) in a single reaction step by carrying out the addition of the acid at a temperature from 90 to 127° C., preferably from 95 to 115° C. If the reaction is carried out in this way, a liquid two-phase system which separates into a lower organic phase and an upper aqueous phase is formed directly.

In step c), the organic phase is separated from the aqueous phase. The organic phase comprises the benzoic acid derivative, water and, if used, organic acid.

The organic phase can be used directly for further processing.

However, the organic phase may be dewatered in step d) prior to further processing. The dewatering is carried out by distilling off the water and remaining organic acid. If acetic acid is used as organic acid in the neutralization step a), the water may also be removed by distilling off some or all of the acetic acid.

The process according to the invention can be carried out continuously and batchwise, and at atmospheric pressure, superatmospheric pressure and reduced pressure.

In the process according to the invention, the yield of 3-[2-chloro-4-(trifluoromethyl)phenoxy]benzoic acid in the organic phase is very high. The aqueous phase which has been removed contains less than 3%, preferably less than 2%, of this compound.

In this isolation process, the handling of solids is dispensed with and the dewatered melt of the 3-[2-chloro-4-(trifluoromethyl)phenoxy]benzoic acid can be employed directly for preparing acifluorfen, 5-[2-chloro-4-(trifluoromethyl)-phenoxy]-2-nitrobenzoic acid, by nitration.

EXAMPLE 1

2500 parts of a 20% strength solution (by weight, based on the free acid) of the potassium salt of 3-[2-chloro-4-(trifluoromethyl)phenoxy]benzoic acid (1.58 mol) of pH 8.8 in a stirred heatable 3 liter glass vessel are diluted with 498 parts of water and heated to 50° C. At this temperature, 370 parts (6.17 mol) of acetic acid are then added within 90 minutes with stirring, causing the 3-[2-chloro-4-(trifluoromethyl)phenoxy]benzoic acid to precipitate. The pH of the resulting suspension is 4.3. The suspension is then heated to 96° at which the solid melts and a two-phase liquid mixture is formed. After the stirrer has been switched off, the phases separate; the lower brown organic melt phase weights, after the aqueous phase has been removed, 594 parts and contains in addition to 84.0 parts of 3-[2-chloro-4-(trifluoromethyl)phenoxy]benzoic acid 12.9 parts of water and 2.33 parts of acetate as free acid or as potassium slat. The aqueous phase only contains <0.1% of 3-[2-chloro-4-(trifluoromethyl)phenoxy]benzoic acid.

EXAMPLE 2

2500 parts of a 20% strength solution (by weight, based on the free acid) of the sodium salt of 3-([2-chloro-4-(trifluoromethyl)phenoxy]benzoic acid (1.58 mol) of pH 8.8 in a stirred heatable 3 liter glass vessel are diluted with 498 parts of water and heated to 50° C. At this temperature, 360 parts (6.0 mol) of acetic acid are then added within 90 minutes with stirring, causing the 3-[2-chloro-4-(trifluoromethyl)phenoxy]benzoic acid to precipitate. The pH of the resulting suspension is 4.3. The suspension is then heated to 100° C. at which the solid melts and a two-phase liquid mixture is formed. After the stirrer has been switched off, the phases separate; the lower brown organic melt phase weights, after the aqueous phase has been removed, 485 parts and contains in addition to 82.5% by weight of 3-[2-chloro-4-(trifluoromethyl)phenoxy]benzoic acid 14.5% by weight of water and 2.5% by weight of acetate as free acid or as sodium salt. The aqueous phase only contains <0.1% of 3-[2-chloro-4-(trifluoromethyl)phenoxy]benzoic acid.

We claim:

1. A process for the isolation of 3-[2-chloro-4-(trifluoromethyl)phenoxy]benzoic acid of the formula I

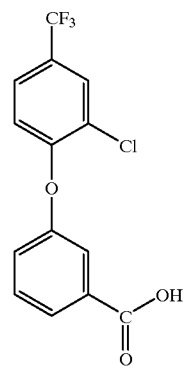

from an aqueous solution of its metal salt, which comprises
  a) reacting the metal salt of 3-[2-chloro-4-(trifluoromethyl)phenoxy]benzoic acid with an organic or inorganic acid;
  b) heating the reaction mixture until a liquid two-phase system of organic and aqueous phase has formed; and
  c) separating the organic phase from the aqueous phase.

2. The process as claimed in claim 1, wherein steps a) and b) are combined in one reaction step.

3. The process as claimed in claim 1, wherein the organic phase of step c) is dewatered in an additional step d).

4. The process as claimed in claim 1, wherein the metal salt used is a sodium or potassium salt.

5. The process as claimed in claim 1, wherein the organic acid used is formic acid, acetic acid, propionic acid or mixtures thereof.

6. The process as claimed in claim 5, wherein the organic acid used is acetic acid.

7. The process as claimed in claim 1, wherein the inorganic acid used is hydrochloric acid, sulfuric acid, phosphoric acid, nitric acid or mixtures thereof.

8. The process as claimed in claim 1, wherein sufficient organic or inorganic acid is added in step a) to obtain a pH of less than 5.

9. The process as claimed in claim 1, wherein the reaction mixture in step b) is heated to at least 90° C.

10. The process as claimed in claim 9, wherein the reaction mixture is heated to at least 96° C.

11. The process as claimed in claim 3, wherein the organic phase is dewatered in step d) by distilling off the water.

12. The process as claimed in claim 6, wherein the organic phase of step c) is dewatered in an additional step d) by distilling off acetic acid.

* * * * *